United States Patent [19]

Bhagwat et al.

[11] Patent Number: 5,126,127
[45] Date of Patent: Jun. 30, 1992

[54] STABILIZED PVP-I SOLUTIONS

[75] Inventors: Dileep Bhagwat, Peekskill; Benjamin Oshlack, New York, both of N.Y.

[73] Assignee: Euroceltique, S.A., Luxembourg, Luxembourg

[21] Appl. No.: 730,462

[22] Filed: Jul. 16, 1991

[51] Int. Cl.$^5$ ............................................. A61K 31/74
[52] U.S. Cl. ............................ 424/78.25; 424/427; 424/437; 424/78.24; 424/667; 424/668; 424/669; 424/670; 424/671; 424/672
[58] Field of Search ............ 424/78, 80, 150, 427, 424/437, 667, 668, 669, 670, 671, 672, 78.25, 78.24

[56] References Cited

U.S. PATENT DOCUMENTS

| | | | |
|---|---|---|---|
| 4,364,929 | 12/1982 | Sasmor et al. | 424/80 |
| 4,401,651 | 8/1983 | Knutson | 424/80 |
| 4,526,751 | 7/1985 | Gartner | 422/37 |
| 4,976,969 | 12/1990 | Plamondon | 424/672 |

Primary Examiner—Thurman K. Page
Assistant Examiner—Louis A. Piccone
Attorney, Agent, or Firm—Steinberg & Raskin

[57] ABSTRACT

Povidone-Iodine (PVP-I) solutions stable according to U.S.P. standards and a method for preparing the same are disclosed. The PVP-I solution includes a microbicidal effective amount of available iodine and an alkalinizing agent in an effective amount to maintain the stability of the solution for a desired shelf-life of the solution when said solution is stored in a substantially nonpermeable container, the solution being non-buffered. In preferred embodiments, the iodophor solution is a microbicidal PVP-I solution for ophthalmic use.

23 Claims, No Drawings

STABILIZED PVP-I SOLUTIONS

BACKGROUND OF THE INVENTION

The present invention is related to stabilized povidone-iodine solutions and a novel method of preparing the same. The present invention is further related to microbicidal ophthalmic preparations comprising povidone-iodine.

Povidone-iodine (polyvinylpyrrolidine-iodine or PVP-I) U.S.P. (U.S. Pharmacopeia) is the raw material used in the preparation of all PVP-I containing formulations.

Provione-iodine is a complex of iodine with povidone. It contains not less than 9.0% by weight, and not more than 12% by weight of available-iodine (titratable iodine) calculated on a dry basis. Povidone Iodine USP has a specification for iodide ion of not more than 6.6% by weight on a dry basis.

PVP-I solutions, as well as other iodophor solutions, have been packaged for medicinal use, e.g. in soft plastic bottles or containers, which can be used for various medicinal purposes, e.g. douching. However, a severe problem that has been encountered with such packaged iodophor solutions, is that elemental iodine (equilibrium iodine) has leached through the packaging itself. In the past, this resulted both in a decrease in stability and medicinal capacity of the iodophor solution contained within the packaging, and made it difficult to handle such packaging since the elemental iodine which leached therethrough caused staining and burning if touched.

The problems associated with packaging such PVP-I solutions in soft plastic bottles o containers have been overcome through the addition of other stabilizers or iodine donating species such as iodate salts, as disclosed in U.S. Pat. No. 4,113,857 (Shetty), and the use of iodide salts, as disclosed in U.S. Pat. No. 4,996,048 (Bhagwat et al.)

In Bhagwat et al., for example, the iodophor solution itself preferably comprises about 0.01-0.03% of iodide therein, in addition to the additional amount of iodide that has been introduced which improves the stability of the iodophor and minimizes leaching of iodine through the packaging. As disclosed therein, at least about 0.01% by weight of the additional iodide, based on the iodophor solution, and up to about 4.0% of the additional iodide is introduced into the packaging. The additional iodide is preferably KI.

Although PVP-I solutions are known to exert microbicidal activity, stabilizing PVP-I solutions for ophthalmic use was problematic prior to the present invention, and in view of the stability problems associated with dilute PVP-I solutions, it has not been possible to date to provide an acceptable formulation of dilute PVP-I solutions, such as for ophthalmic use. For example, the introduction of donating species such as iodate into a PVP-I solution is not considered to be desirable when the solution is to be used as an ophthalmic preparation because iodate (and probably iodide) are known to be irritating and toxic to the pigment epithelium of the retina. Thus, a PVP-I solution stabilized via the addition of, for example, potassium iodide and/or potassium iodate would not be useful as an ophthalmic preparation.

It is generally recognized that an ophthalmic solution should have the same pH as human lacrimal fluid. Such a result can be obtained for an ophthalmic preparation via the use of a buffer system approaching physiological pH. It is common practice to control the pH of solutions through the use of buffers, which are pairs of related chemical compounds capable of resisting large changes in the pH of a solution caused by the addition of small amounts of acid or base, regardless of the source. For example, borate buffers (which comprise weak acids and their conjugate bases) have been used in ophthalmic preparations.

Historically, PVP-I solutions have been buffered to at least a pH of 5. This prior art is a known requirement for physiological compatibility and stability of aqueous PVP-I solutions. It has also long been recognized in the art that the more dilute the PVP-I solution, the less stable it is.

It has been found that for dilute concentrations of PVP-I which are microbicidal, especially those concentrations of PVP-I which would be useful in ophthalmic preparations, the use of buffers do not stabilize the solution. For example, if a 0.3% PVP-I solution buffered at a pH of 5.4 is prepared without the use of stabilizers or iodine donating species, the stability of such solutions in glass bottles cannot be maintained.

It is therefore an object of the present invention to provide a novel stabilized solution of an iodophor, most particularly PVP-I, which can be stored in nonpermeable containers, such as glass bottles.

It is another object of the present invention to provide a novel stabilized microbicidal solution of PVP-I which can be stored in glass bottles and which is useful as an ophthalmic preparation.

It is a further object of the present invention to provide a novel stabilized microbicidal ophthalmic preparation containing a dilute solution of PVP-I which can be stored in glass bottles and which is not irritating or toxic to the eye.

It is a further object of the present invention to provide a method of using a PVP-I solution as an antimicrobial for ophthalmic use.

It is a further object of the present invention to provide a process for preparing a dilute PVP-I solution which is effective as a microbicidal for ophthalmic use and which is stable when stored in glass bottles.

It is a further object of the present invention to provide a method of treating the eye via the use of a microbicidal stabilized ophthalmic solution comprising PVP-I.

SUMMARY OF THE INVENTION

The above-mentioned objects and others are attained by the present invention, which is related to stabilized, microbicidal iodophor solutions which can be stored in a suitable nonpermeable containers.

More particularly, the present invention is related to a stable iodophor solution, such as according to U.S.P. or F.D.A. standards, comprising a microbicidal effective amount of available iodine which amount is insufficient by itself to render the iodophor solution stable (such as with respect to U.S.P. standards), and a suitable alkalinizing agent in an amount effective to maintain said amount of available iodine within acceptable limits during its stated shelf-life, for example, to maintain said amount of available iodine at a minimum of about 85% and a maximum of 120% of an initial amount of available iodine in the solution under accelerated aging conditions. The accelerated aging conditions may comprise, for example, subjecting the solution to elevated temperatures, e.g. from about 35° to about 40° C., for about three months when the solution is stored in a glass or other suitably nonpermeable container, the solution being non-buffered.

In a preferred embodiment, the iodophor solution comprises a non-irritating ophthalmic solution which is microbicidal and stable according to U.S.P. standards but which solution is not buffered. In this embodiment the alkalinizing agent in the effective amount is non-toxic and non-irritating to the eye. Preferably, a sufficient amount of an agent is included to render the solution substantially isotonic to human lacrimal fluid.

In preferred embodiments, the iodophor solution comprises povidone-iodine.

In other preferred embodiments, the present invention is related to a substantially non-irritating povidone-iodine ophthalmic solution comprising povidone-iodine in an initial amount of available iodine of from about 0.03% to about 0.06%, which solution is microbicidal and non-buffered.

The present invention is further related to an iodophor solution stable according to U.S.P. standards, comprising a microbicidal effective amount of available iodine which is insufficient by itself to render said iodophor solution stable according to U.S.P. standards, and an alkalinizing agent in an amount effective to provide said solution with an initial pH of from about 2 to about 6.5, such that the solution is stable according to U.S.P. standards, the solution being non-buffered.

The present invention is also related to a method of preparing a povidone-iodine solution which is stable according to U.S.P. standards when stored in a glass container. In this method, povidone-iodine is provided in an effective amount of available iodine to render the solution microbicidal. A suitable alkalinizing agent is added in an amount effective to maintain the amount of available iodine at a minimum of about 85% and a maximum of 120% of an initial amount of said available iodine for about three months at a temperature of about 40° C. when the ophthalmic solution is stored in a glass container, and the solution is non-buffered.

In another method of the present invention, the povidone iodine solution is intended for use as an ophthalmic preparation, and the alkalinizing agent in the said effective amount is non-toxic and non-irritating.

The present invention is also related to a process for treating the eye with a microbicidal treatment which is stable according to U.S.P standards. A povidone-iodine solution having an effective amount of available iodine to render the solution microbicidal but which in said amount is by itself insufficient to render the solution stable according to U.S.P. standards is prepared, and a suitable alkalinizing agent is added in an amount effective to maintain said amount of available iodine at a minimum of about 85% and a maximum of 120% of an initial amount of said available iodine for about three months at a temperature of about 40° C. The alkalinizing agent in the said effective amount is non-toxic and non-irritating, and the solution is non-buffered. The solution is rendered substantially isotonic to human lacrimal fluid, and stored in a glass container for at least three weeks. Thereafter, the eye is treated with the microbicidal solution by placing a sufficient amount of the solution onto the external surface of an eye.

DETAILED DESCRIPTION OF THE INVENTION

The combination of elemental iodine and certain organic polymers, e.g. polyvinylpyrrolidone and detergent polymers, have bee termed iodophor. The organic polymers used to form an iodophor comprise a broad range of molecular weight and chain length, and may be either ionic or non-ionic in characters, as well as possessing either surfactant or non-surfactant properties. A loose bond forms between the iodine and organic polymer to form a complex. Aqueous solutions of up to about 30% in iodine content, may be prepared.

The general method for the preparation of a iodophor complex is to bring into intimate contact, elemental diatomic iodine with the selected polymer, either in the dry or powder form or in the presence of a suitable solvent. Heat may be used to accelerate complex formation. Upon completion of the reaction, the iodophor complex of the respective polymeric carrier with iodine is obtained in certain reproducible proportions of one to the other.

The iodophor preparation can then be introduced in any convenient manner into the appropriate packaging, for purposes of the present invention, preferably glass containers (e.g., bottles).

While PVP-I is the preferred iodophor, the present invention is applicable to any iodine-releasing material. With regard to embodiments of the present invention directed to ophthalmic solutions, the iodine-releasing material, must of course be one that is suitable, i.e., non-toxic and non-irritating.

For example, with regard to other embodiments of the present invention not directed to ophthalmic preparations, other iodophor complexes comprise non-ionic, cationic and anionic detergent carriers. A detailed discussion of these materials is found in U.S. Pat. No. 4,996,048 (Bhagwat et al.), hereby incorporated by reference.

Examples of iodide salts which can be added to such iodophor preparations include sodium iodide, potassium iodide, calcium iodide and zinc iodide, with potassium iodide specifically being preferred.

Iodophor preparations are described in terms of available or titratable iodine which is considered to be the iodine released from the complex to exert germicidal action thereof. However, such available iodine determinations do not reflect either the total iodine content of the iodophor, or its germicidal potency. The iodine moiety of polyvinylpyrrolidone (povidone)-iodine complex is present in an aqueous iodophor solution in the form of different thermodynamically stable anionic iodine species and diatomic iodine. The anionic iodine forms are capable of generating diatomic iodine in the course of their respective equilibrium reactions The anionic species do not distribute themselves into an extracting solvent which removes only the nonionic iodine. Such iodine is generated in the course of the iodine equilibrium reaction and extraction thereof by a solvent fractionates the equilibrium state. The disturbed equilibrium reaction is soon re-established to restore new anionic iodine species, but now at a different concentration level since the previous aqueous iodine content of the solution has been reduced by the extracting solvent.

Since the iodophor iodine exerting microbicidal actions exists in solutions in dynamic equilibrium with ionic iodine species, removal of one or more of the iodine species results in formations of new equilibrium forms. An extracting solvent removes or consumes iodine from the iodophor solution in a manner similar to that of a microbial and organic load during degerming use of the iodophor solution. The amount of iodine available for germicidal action in an iodophor preparation therefore is the amount of iodine in equilibrium in the solution at the time of use. Such equilibrium iodine content represents the germicidal potency of the preparation, but not the total iodine content titrated for the preparation nor the apparent distribution of the iodine forms. Although iodophor solutions have been assayed in the art for available or titratable iodine, it is the equilibrium iodine which is the particular form of iodine present in the iodophor solution that is instantly available to exert microbicidal action. This form of iodine differs from titratable iodine and the other iodine species present in the iodophor solution. Therefore, the equilibrium iodine content of an iodophor solution is to be distinguished from its titratable iodine content.

The titratable iodine content of a iodophor preparation includes the iodine reservoir of the iodophor preparation (povidone iodine), as well as the equilibrium iodine in solution.

Titratable iodine = Reservoir Iodine + Equilibrium Iodine

However, it is the equilibrium iodine alone that exerts the microbicidal action of the preparation at any given moment. The portion of the titratable iodine content remaining after subtracting the amount of equilibrium iodine present, serves as the iodine reservoir to generate new equilibrium iodine in solution as it is consumed by the microbial and bio-organic load in the course of microbicidal activity, but does not exert such germicidal action by itself.

The level of iodide ions inherently present in any PVP-I formulation using PVP-I raw material, therefore depends on the amount of iodide ion present in the raw material PVP-I used. For example, on a theoretical basis, if the PVP-I contains 6% by weight iodide ion, then a formulation containing 10% by weight of PVP-I would contain 0.6% by weight iodide ions. However, PVP-I raw material containing a level of iodide ion greater than specification of U.S. Pharmacopeia, could also be used in formulating a PVP-I containing product.

Thus, the minimum amount of iodide ion inherently present in a PVP-I formulation could be as low as 0.0% by weight, while the maximum amount of iodide ion inherently present in such a PVP-I formulation would be the amount contributed by the PVP-I raw material used to formulate the same. For example, on a theoretical basis, if a formulation contains 0.36% by weight PVP-I, and the PVP-I contains the maximum iodide allowable of 6.6% by weight, then the formulation will have 0.0237% by weight iodide present.

Typically, for PVP-I containing products, the U.S. Pharmacopeia (U.S.P.) allows a 20% overage (i.e., 120%) from label claim and requires a minimum 85% of label at the end of the stated product shelf-life, for example, as determined by accelerated aging (3 months/40° C.) of the product. This translates into an allowable drop of 35%. Therefore, for 0.3% PVP-I solutions, the maximum allowable limit is 0.36% PVP-I and the minimum is 0.25%. Thus, stability of a 0.30% solution should be above 0.25% PVP-I (or 0.025% available iodine) to be considered stable.

Generally, PVP-I solutions having a concentration greater than 1.0% are relatively stable in glass or other nonpermeable packaging. However, such a concentration of PVP-I is not suitable for many uses. For example, with regard to ophthalmic preparations, a concentration of PVP-I of 1.0% or greater is not desirable in ophthalmic preparations because such concentrations are irritating to the eye.

It has now been surprisingly discovered that when PVP-I solutions at dilute concentrations are not buffered, e.g. to a pH of about 5.6, but instead only adjusted to a suitable pH via the addition of a suitable alkalinizing agent, e.g. to a pH of about 4.0, without the use of buffers, the stability of the PVP-I solution was maintained for a period of 3 years in glass bottles, using the U.S.P. allowable overage of 20% extra PVP-I.

Preferably, the PVP-I solution has a minimum concentration of 0.3% (0.03% available iodine) in order to maintain the stability of the solution according to U.S.P. stability standards. It has now surprisingly been further found that lower PVP-I concentrations, even as low as 0.2%, are as effective as known marketed products such as Neosporin ® and Garamycin ® eye drops, and that PVP-I solutions having concentrations as low as 0.12% (0.012% available iodine) are also effective as antimicrobials. Although at such concentrations the iodophor solutions of the present invention are not stable according to U.S.P. standards, the iodophor solutions of the present invention at such concentrations are surprisingly and substantially more stable than prior art iodophor solutions at such concentrations, and therefore are useful nonetheless where compliance with U.S.P. standards is not of concern.

For use as an ophthalmic preparation, the stabilized microbicidal solutions of the present invention preferably comprise from about 0.12% to about 0.72% PVP-I. A higher concentration of PVP-I may be used, the limiting factor, among other things, being that the ophthalmic solution should not be unduly irritating to the eye. The limiting factor for lower concentrations of PVP-I solutions, among other things, is stability and efficacy as a microbicidal.

As explained above, the PVP-I solutions of the present invention are stabilized by adding a suitable alkalinizing agent. The amount of alkalinizing agent needed is that amount which is effective to maintain the amount of available iodine at a minimum of about 85% and a maximum of 120% of an initial amount of said available iodine for about three months at a temperature of about 40° C. when the solution is stored in a glass container. The solution is non-buffered.

When the solution is prepared as an ophthalmic preparation, the alkalinizing agent in the said effective amount is non-toxic and preferably non-irritating. Any such alkalinizing agent known in the art which may be used in ophthalmic preparations in the said effective amount may be used in the present invention. In preferred embodiments, the alkalinizing agent preferably comprises sodium hydroxide, potassium hydroxide, sodium bicarbonate, disodium phosphate, mixtures of any of the foregoing, or the like. An especially preferred alkalinizing agent is sodium hydroxide.

In embodiments of the present invention where the stabilized iodophor solution is not intended for ophthalmic use, the choice of alkalinizing agent is, of course, not as critical with respect to toxicity and irritating properties. In such embodiments, any alkalinizing agent known in the art may be used, depending upon the intended use of the product.

In general, the pH of a dilute PVP-I solution, i.e. a PVP-I solution having a concentration of about 1.0% has a pH of about 2, and a 0.3% PVP-I solution has a pH of about 2.7. Thus, the pH of a dilute PVP-I solution is dependent upon the concentration of the PVP-I. The pH of the PVP-I solution is adjusted via the addition of the alkalinizing agent until a pH of from about 2 to about 6.5 is attained, preferably at least until a stabilized product is obtained according to U.S.P. standards. More preferably, the alkalinizing agent is added to the PVP-I solution until a pH of from about 2 to about 4.5 is obtained. It is especially preferred that the alkalinizing agent (i.e., sodium hydroxide) is added in a amount effective to adjust the pH of the PVP-I solution to a pH of from about 4 to about 4.5.

The pH of normal tear (lacrimal) fluid is about 7.4, although the pH of the film of tears in contact with the surface of the eye may higher, i.e. from 7.4–8.0, because of loss of carbon dioxide to the atmosphere. It has been reported that an uncomfortable condition exists when the pH is under 6 or over 8, but the eye is more sensitive to acid than to alkaline solutions. The eye has also been reported to tolerate isotonic solutions more alkaline than tear fluid better than it does isotonic solutions that are acid. The tear fluid itself has a certain buffer capacity, although it is not sufficiently strong to avoid discomfort when solutions of more strongly acidic drugs are applied.

Unexpectedly, it has been discovered that the stabilized, microbicidal PVP-I ophthalmic solutions of the present invention are substantially non-irritating to the eye despite the fact that these solutions are not buffered and generally have a pH in the acidic range, e.g. pH 4.

Lacrimal fluid has an isotonicity value approximately the same as that of a 0.9% sodium chloride solution. An ophthalmic solution which is isotonic with lacrimal fluid causes less discomfort than one that is hypotonic or hypertonic. It is therefore especially preferred that the opthalmic preparations of the present invention be adjusted with a suitable agent so that they are isotonic with the eye (i.e., with human lacrimal fluid). An especially preferred agent is sodium chloride.

Antimicrobials are usually required in ophthalmic solutions. A suitable antimicrobial preservative should have a wide bacteriostatic, or bacteriocidal activity against organisms; must maintain its microbial properties during storage, etc. have a rapid action, be nonallergenic and nonsensitized; have rapid action: be non-toxic and non-irritating; be chemically and pharmacologically compatible with other ingredients of the system; be chemically stable and not undergo discoloration; and should be readily and adequately soluble in the appropriate vehicles.

The stabilized PVP-I solutions of the present invention posses the beneficial properties outlined above. The stabilized PVP-I solutions of the present invention when prepared in suitable concentrations for opthalmic use, have microbicidal activity as effective as that of commercially available antibiotic solutions such as Neosporin ® and Garamycin ®, and are similar to such products with respect to their non-irritating properties. Thus, it is contemplated that the stabilized microbicidal PVP-I solutions of the present invention are useful as microbicidal ophthalmic preparations, as combination products (e.g. in combination with local anesthetics, anti-inflammatories, etc.) for example, for ophthalmic and otic use. It is also contemplated that the stabilized PVP-I solutions of the present invention are useful in ophthalmic products and the like as a preservative.

Preferably, the containers for storing the iodophor solutions of the present invention are comprised of substantially nonpermeable materials. By "substantially nonpermeable", it is meant that the material comprising the packaging does not allow a substantial amount of elemental iodine (such as that available as equilibrium iodine from an iodophor solution) to leach through the packaging itself. Examples of suitable containers include those comprised of glass, high density polyethylene, fluorinated high density polyethylene, and other specially treated plastics which treatments render the plastics substantially nonpermeable. The glass containers for storing the iodophor solutions of the present invention are those which are composed of pharmaceutically acceptable glass, as defined in the U.S. Pharmacopeia or National Formulary (N.F.). Both the U.S.P. and N.F. define the same four glass types (highly resistant, borosilicate glass, treated soda-lime glass, soda-lime glass, and general purpose soda-lime glass) and their alkalinity limits. The glass containers may be colorless, opaque or colored. There are four types of clear containers available, colorless, green, blue and amber. Amber glass is most preferred.

DETAILED DESCRIPTION OF THE PREFERRED EMBODIMENTS

The following examples illustrate various aspects of the present invention. They are not to be construed to limit the claims in any manner whatsoever. The percentage of ingredients for each example provided below are expressed as percentage weight/volume, unless otherwise indicated. The percent available iodine for each example provided below was determined by the method described in U.S. Pharmacopia XXI under povidone iodine topical solution (page 864).

EXAMPLE 1

In order to determine the stability of a buffered, dilute solution of PVP-I, the following 0.3% PVP-I solution, isotonic and buffered at a pH of 5.6, is prepared without the use of stabilizers or iodine donating species:

TABLE 1

| 0.3% PVP-I Solution - Buffered, Isotonic | |
|---|---|
| Ingredient | Percentage |
| PVP-I* | 0.3 |
| Igepal CO-630 | 0.004 |
| Methocel E4M | 0.5 |
| Monobasic Sodium Phosphate | 0.76 |
| Dibasic Sodium Phosphate | 0.47 |
| Sodium Chloride | 0.5 |
| Sodium Hydroxide (5%) | qs to pH 5.6 |
| Purified Water | qs to 100 |

*(plus 0.06% U.S.P. allowable overage)

Accelerated stability studies were conducted for the above formulation. In order to remain within the definition of stability for a PVP-I solution as defined in the USP for 0.3% PVP-I solutions, the maximum allowable limits for the above formulation was 0.36% PVP-I and minimum was 0.25% PVP-I. Thus, stability of a 0.30% solution should be above 0.25% PVP-I (or 0.025% available iodine) to be considered stable. The formulation fell below this level after three months at room temperature, and after one month at 40° C. and 80% relative humidity. Therefore, the stability of these solutions in glass bottles cannot be maintained.

EXAMPLE 2

A non-isotonic 0.3% PVP-I solution was prepared which was not buffered at the above pH of 5.4, but only with adjusting the pH at 4.0. The formula for this solution was as follows:

TABLE 2

0.3% PVP-I, NON-BUFFERED, NON-ISOTONIC

| Ingredient | Percent |
|---|---|
| PVP-I* | 0.30 |
| Igepal CO-630 | 0.004 |
| Methocel E4M | 0.5 |
| Sodium Hydroxide | qs to pH 4.0 |
| Purified water | qs to 100 |

*(plus 0.06% U.S.P. allowable overage)

Three batches of the above formula were made and tested for stability. The results are provided in Table 3 below.

TABLE 3

| Testing Time | Available Iodine (% w/v) (0.025–0.036%) | pH (2.5–4.5) | Appearance | Viscosity (10–30 cps) |
|---|---|---|---|---|
| Batch 1 - Betadine Ophthalmic Drops | | | | |
| Initial | 0.036% | 4.44 | Clear viscous brown color | 25.3 |
| Room Temperature | | | | |
| 3 mos | 0.035% | 4.06 | no change | 24.3 |
| 6 mos | 0.035% | 3.99 | no change | — |
| 9 mos | 0.032% | 3.89 | no change | — |
| 12 mos | 0.033% | 3.97 | no change | 22.1 |
| 18 mos | 0.034% | 3.70 | no change | — |
| 24 mos | 0.031% | 3.78 | no change | 24.8 |
| 36 mos | 0.028% | 3.55 | no change | 19.4 |
| 37° C., 80% Relative Humidity | | | | |
| 1 mos | 0.032% | 3.90 | no change | 21.0 |
| 2 mos | 0.031% | 3.83 | no change | — |
| 3 mos | 0.031% | 3.80 | no change | 22.4 |
| Batch 2 - Betadine Ophthalmic Drops | | | | |
| Initial | 0.036% | 4.36 | Clear viscous brown color | 21.8 |
| Room Temperature | | | | |
| 3 mos | 0.034% | 4.09 | no change | 23.0 |
| 6 mos | 0.035% | 3.96 | no change | — |
| 9 mos | 0.031% | 3.88 | no change | — |
| 12 mos | 0.030% | 3.82 | no change | 20.8 |
| 18 mos | 0.029% | 3.80 | no change | — |
| 24 mos | 0.025% | 3.73 | no change | 21.9 |
| 36 mos | 0.0265% | 3.51 | no change | 22.2 |
| 37° C., 80% Relative Humidity | | | | |
| 1 mos | 0.030% | 3.85 | no change | 19.8 |
| 2 mos | 0.030% | 3.79 | no change | — |
| 3 mos | 0.029% | 3.82 | no change | 21.1 |
| Batch 3 - Betadine Ophthalmic Drops | | | | |
| Initial | 0.036% | 4.35 | Clear viscous brown color | 21.1 |
| Room Temperature | | | | |
| 3 mos | 0.035% | 4.08 | no change | 22.4 |
| 6 mos | 0.033% | 3.81 | no change | — |
| 9 mos | 0.032% | 3.84 | no change | — |
| 12 mos | 0.031% | 3.86 | no change | 20.2 |
| 18 mos | 0.030% | 3.8 | no change | — |
| 24 mos | 0.027% | 3.69 | no change | 20.8 |
| 36 mos | 0.0265% | 3.49 | no change | 18.9 |
| 37° C., 80% Relative Humidity | | | | |
| 1 mos | 0.031% | 3.80 | no change | 20.2 |
| 2 mos | 0.029% | 3.73 | no change | — |
| 3 mos | 0.027% | 3.75 | no change | 19.2 |

Surprisingly, it was discovered that stability of the PVP-I solution was maintained for a period of 3 years, in amber glass bottles, using the USP allowable overage of 20% extra PVP-I.

EXAMPLE 3

Further studies were conducted in order to determine the effect upon stability when the 0.3% PVP-I solutions were adjusted to isotonicity. The formula tested is set forth in Table 4 as follows:

TABLE 4

0.3% PVP-I, Non-buffered, Isotonic

| Ingredient | Percent |
|---|---|
| PVP-I* | 0.30 |
| Igepal CO-630 | 0.004 |
| Methocel E4M | 0.50 |
| Sodium Chloride | 0.85 |
| Sodium Hydroxide | qs to pH 4.0 |
| Purified water | qs to 100 |

*(plus 0.06% U.S.P. allowable overage)

Three batches of the above formula were made and tested for stability. The results are provided in Table 5 below:

TABLE 5

| Testing Time | Available Iodine (% w/v) (0.025–0.036%) | pH (2.5–4.5) | Appearance | Viscosity (10–30 cps) |
|---|---|---|---|---|
| Batch 1 - Betadine Ophthalmic Drops | | | | |
| Initial | 0.036% | 3.92 | clear viscous brown color | 22.4 |
| Room Temperature | | | | |
| 3 mos | 0.036% | 3.83 | pass | 22.4 |
| 6 mos | 0.034% | 3.73 | pass | 22.4 |
| 9 mos | 0.032% | 3.65 | pass | — |
| 12 mos | 0.032% | 3.63 | pass | 19.2 |
| 18 mos | 0.028% | 3.60 | pass | — |
| 24 mos | 0.029% | 3.58 | pass | 19.8 |
| 36 mos | 0.028% | 3.54 | pass | 17.1 |
| 37° C., 80% Relative Humidity: | | | | |
| 1 mos | 0.029% | 3.64 | pass | 18.6 |
| 2 mos | 0.029% | 3.60 | pass | — |
| 3 mos | 0.029% | 3.64 | no change | 17.9 |
| Batch 2 - Betadine Ophthalmic Drops | | | | |
| Initial | 0.035% | 4.04 | clear viscous brown color | 21.4 |
| Room Temperature | | | | |
| 3 mos | 0.035% | 4.00 | pass | 22.4 |
| 6 mos | 0.033% | 3.89 | pass | — |
| 9 mos | 0.032% | 3.83 | pass | — |
| 12 mos | 0.030% | 3.79 | pass | 19.5 |
| 18 mos | 0.031% | 3.70 | pass | — |
| 24 mos | 0.028% | 3.62 | pass | 19.7 |
| 36 mos | 0.028% | 3.51 | pass | 17.7 |
| 37° C., 80% Relative Humidity: | | | | |
| 1 mos | 0.031% | 3.81 | pass | 19.2 |
| 2 mos | 0.031% | 3.72 | pass | — |
| 3 mos | 0.030% | 3.78 | pass | 19.2 |
| Batch 3 - Betadin Ophthalmic Drops | | | | |
| Initial | 0.036% | 4.08 | clear viscous brown color | 21.1 |
| Room Temperature | | | | |
| 3 mos | 0.034% | 3.92 | pass | 21.8 |
| 6 mos | 0.034% | 3.77 | pass | — |
| 9 mos | 0.032% | 3.69 | pass | — |
| 12 mos | 0.034% | 3.67 | pass | 19.5 |
| 18 mos | 0.031% | 3.60 | pass | — |
| 24 mos | 0.030% | 3.59 | pass | 19.8 |
| 36 mos | 0.029% | 3.44 | pass | 16.0 |
| 37° C., 80% Relative Humidity: | | | | |
| 1 mos | 0.032% | 3.71 | pass | 18.6 |
| 2 mos | 0.031% | 3.62 | pass | — |
| 3 mos | 0.030% | 3.67 | pass | 19.2 |

As can be ascertained from the results set forth above, stability was not compromised by rendering the PVP-I solution isotonic.

Another study was conducted using the formula presented in Table 4 and packaged in plastic bottles. In Comparative Batch 1, a polypropylene container was used. In Comparative Batch 2, a low density polyethylene container was used. The results of stability testing are set forth in Table 6 below.

TABLE 6

| Comparative Batch 1 - Betadine Ophthalmic Drops | | | | |
|---|---|---|---|---|
| Testing Time | Available Iodine (% w/v) (0.025–0.036%) | pH (2.5–4.5) | Appearance | Viscosity (10–30 cps) |
| Initial | 0.036% | 3.90 | clear red-brown solution free of particulate matter | 15.36 |
| 37° C., 80% Relative Humidity: | | | | |
| 1 mos | 0.021% | 3.52 | light amber solution | — |
| 2 mos | 0.013% | 3.24 | light amber solution | — |
| Comparative Batch 2 - Betadine Ophthalmic Drops | | | | |
| Testing Time | Available Iodine (% w/v) (.025–.036%) | pH (2.5–4.5) | Appearance | Viscosity (10–30 cps) |
| Initial | 0.036% | 3.90 | clear red-brown solution free of particulate matter | 15.36 |
| 37°πC., 80% Relative Humidity: | | | | |
| 1 mos | 0.004 | 3.50 | very light yellow amber | — |
| 2 mos | 0.002 | 3.23 | very light yellow amber | — |

Stability of Comparative Batches 1 and 2 stored in plastic bottles was not even maintained after one month since all the solutions became colorless (indicating the PVP-I was lost).

EXAMPLES 4–6

Further investigations were conducted at different concentrations of PVP-I solutions packaged in amber glass bottles. The solutions made are set forth in Table 7 as follows:

TABLE 7

| Ingredient | % | % | % |
|---|---|---|---|
| PVP-I | 0.2* | 0.4* | 0.5* |
| Igepal CO-630 | 0.004 | 0.004 | 0.004 |
| Methocel E4M | 0.4 | 0.4 | 0.4 |
| Sodium Chloride | 0.85 | 0.85 | 0.85 |
| Sodium Hydroxide | qs to pH 4.0 | qs to pH 4.0 | qs to pH 4.0 |
| Purified water | qs to 100 | qs to 100 | qs to 100 |

*Plus a 20% overage, which is the maximum USP allowable overage.

Batches of the above formula were made and tested for stability. The results are provided in Table 8 below:

TABLE 8

| PVP-I, Non-buffered, Isotonic 0.2% PVP-I Ophthalmic Drops | | | | |
|---|---|---|---|---|
| Testing Time | Available Iodine (% w/v) (0.017–0.025%) | pH (2.5–4.5) | Appearance | Viscosity (10–30 cps) |
| Initial | 0.025% | 3.90 | clear reddish brown solution free of particulate matter | 11.61 |
| Room Temperature | | | | |
| 3 mos | 0.021% | 3.80 | no change | 12.80 |
| 6 mos | 0.023% | 3.78 | no change | — |
| 9 mos | 0.019% | 3.70 | no change | — |
| 12 mos | 0.021% | 3.60 | no change | — |
| 18 mos | 0.019% | 3.60 | no change | — |
| 24 mos | 0.016% | 3.56 | no change | — |
| 36 mos | 0.017% | 3.59 | no change | — |
| 37° C. | | | | |
| 1 mos | 0.020% | 3.78 | no change | — |
| 2 mos | 0.019% | 3.69 | no change | — |
| 3 mos | 0.017% | 3.63 | no change | 11.52 |
| 0.4% PVP-I Ophthalmic Drops | | | | |
| Testing Time | Available Iodine (% w/v) (0.034–0.048%) | pH (2.5–4.5) | Appearance | Viscosity (10–30 cps) |
| Initial | 0.048% | 3.83 | clear reddish brown solution free of particulate matter | 11.90 |
| Room Temperature | | | | |
| 3 mos | 0.044% | 3.71 | no change | 12.16 |
| 6 mos | 0.048% | 3.60 | no change | — |
| 9 mos | 0.043% | 3.52 | no change | — |
| 12 mos | 0.042% | 3.50 | no change | — |
| 18 mos | 0.041% | 3.45 | no change | — |
| 24 mos | 0.040% | 3.41 | no change | — |
| 36 mos | 0.0399% | 3.39 | no change | — |
| 37° C. | | | | |
| 1 mos | 0.042% | 3.61 | no change | — |
| 2 mos | 0.042% | 3.55 | no change | — |
| 3 mos | 0.042% | 3.43 | no change | 10.56 |
| 0.6% PVP-I Ophthalmic Drops | | | | |
| Testing Time | Available Iodine (% w/v) (0.0425–0.048%) | pH (2.5–4.5) | Appearance | Viscosity (10–30 cps) |
| Initial | 0.058% | 3.87 | clear reddish brown solution free of particulate matter | 13.70 |
| Room Temperature | | | | |
| 3 mos | 0.056% | 3.90 | no change | 11.52 |
| 6 mos | 0.057% | 3.61 | no change | — |
| 9 mos | 0.054% | 3.52 | no change | — |
| 12 mos | 0.053% | 3.40 | no change | — |
| 18 mos | 0.051% | 3.42 | no change | — |
| 24 mos | 0.048% | 3.37 | no change | — |
| 36 mos | 0.047% | 3.36 | no change | — |
| 37° C. | | | | |
| 1 mos | 0.054% | 3.57 | no change | — |
| 2 mos | 0.053% | 3.55 | no change | — |
| 3 mos | 0.052% | 3.74 | no change | 10.24 |

From the results set forth above, it was observed that the 0.2% solution was only stable for 18 months, while the 0.4% and 0.5% were stable for at least three years.

EXAMPLES 7-10

PVP-I solutions having concentrations of 0 2%, 0.03%, 0.04%, and 0.05% were prepared in accordance with the formulas provided in Examples 3-6. These solutions were then tested for In vitro microbiology against two commercially available products.

Killing time tests were conducted with a series of log phase cultures of gram negative and gram positive organisms including Gentamicin resistant *Pseudomonas aeruoinosa* and selected viruses. Controls used were ophthalmic preparations of Neosporin ® and Garamycin ® (Comparative Examples A and B, respectively). Bacterial samples were taken at 30 seconds, 1, 2, 5, 10 and 15 minutes and transferred into culture media containing inactivators for iodine. Similarly, virus killing time tests were sampled at one minute and transferred into inactivating media. The results obtained are set forth in Table 9 and Table 10:

TABLE 9

BACTERIAL KILLING TESTS

| Example | 7 | 8 | 9 | 10 | A | B |
|---|---|---|---|---|---|---|
| Available Iodine (% w/v) | 0.02 | 0.03 | 0.04 | 0.05 | 0.0 | 0.0 |
| Organic | Killing Time (in seconds unless otherwise noted) | | | | | |
| C. albicans | <30 | <30 | <30 | <30 | <30 | <30 |
| P. mirabilis | <30 | <30 | <30 | <30 | <15 | 3 min |
| Ps. aeruginosa | 2 min | 2 min | <30 | <30 | <30 | 5 min |
| Ps. aeruginosa, Gm+ | 2 min | <30 | <30 | <30 | 10 min | >15 min |
| Ps. aeruginosa, Gm+ | 5 min | <30 | <30 | <30 | >15 min | >15 min |
| Ps. aeruginosa, Gm+ | 1 min | <30 | <30 | <30 | >15 min | >15 min |
| S. aureus | 1 min | <30 | <30 | <30 | >15 min | <30 |
| E. coli | <30 | <30 | <30 | <30 | <30 | 5 min |
| S. pneumoniae | <30 | <30 | <30 | <30 | >15 min | <30 |
| N. gonorrhea | <30 | <30 | <30 | <30 | <30 | <30 |

(anti-bacterial activity = $10^6$ kill of log phase culture at sample time point)

TABLE 10

VIRAL KILLING TESTS

| Example | 7 | 8 | 9 | 10 | A | B |
|---|---|---|---|---|---|---|
| Available Iodine (% w/v) | 0.02 | 0.03 | 0.04 | 0.05 | 0.0 | 0.0 |
| Anti-viral activity Estimation of Virus Kill at 1 Minute Sample Time Point | | | | | | |
| HSV-II | ≧99.999 | ≧99.999 | ≧99.999 | ≧99.999 | ≧99.999 | ≧99.999 |
| Adenovirus 8 | 90 | 0 | 90 | 0 | 0 | 0 |
| Adenovirus 19 | 90 | 90 | 90 | 99 | 90 | 90 |

It was therefore surprisingly further found conducting in-vitro bacterial and viral killing time tests, that low PVP-I concentrations, even as low as 0.2% are as effective as known marketed products as Neosporin ® and Garamycin ® eye drops.

The PVP-I Ophthalmic Drops of Example 8 were tested for ocular safety before the lot was released for human clinical trials. Two vials were taken from sterile vials set aside for clinical trials. A 0.1 ml sample of each tested vial was instilled into one eye of each of six albino rabbits. The animals were observed for 72 hours for signs of ocular corneal or conjunctival irritation. Results obtained at the end of the 72 hour test period found the contents of both test vials to be non-irritating in this standard ocular safety test.

EXAMPLES 11-12

In Examples 11 and 12, a study was conducted similar to that in Examples 7-10 above, with the anti-microbial effect of PVP-I solutions as dilute as 0.12% (Example 11) and as concentrated as 0.60% (Example 12) were determined, respectively. The formulations for these results are set forth in Tables 11 and 12, respectively; and the results are provided in Table 13 below:

TABLE 11

0.12% PVP-I, Non-buffered, Isotonic

| Ingredient | Percent |
|---|---|
| PVP-I | 0.12 |
| Igepal CO-630 | 0.004 |
| Methocel E4M | 0.50 |
| Sodium Chloride | 0.90 |
| Sodium Hydroxide (5%) | qs to pH 4.0 |
| Purified water | qs to 100 |

TABLE 12

0.6% PVP-I, Non-buffered, Isotonic

| Ingredient | Percent |
|---|---|
| PVP-I | 0.60 |
| Igepal CO-630 | 0.004 |
| Methocel E4M | 0.50 |
| Sodium Chloride | 0.90 |
| Sodium Hydroxide (5%) | qs to pH 4.0 |
| Purified water | qs to 100 |

TABLE 13

TEST - In vitro killing

| Organism | Example 11 | Example 12 |
|---|---|---|
| N. gonorrhoea | >15 min. | <30 sec. |
| C. albicans | 1 min | <30 sec. |
| P. Mirabilis | 2 min | <30 sec. |
| Ps. aeruginosa | >15 min. | <30 sec. |
| S. aureus | 3 min. | <30 sec. |
| E. coli | >15 min. | <30 sec. |
| G. vaginale | 5 min. | <30 sec. |
| S. epidermidis | 2 min. | <30 sec. |
| H. simplex II | 3 log kill | 3 log kill |

From the results obtained above, it can be seen that PVP-I solutions at least as dilute as 0.12% PVP-I (0.012% available iodine) and at least as concentrated as 0.060% PVP-I are also effective as an anti-microbial.

EXAMPLES 13-15

In Examples 13 and 14, rabbit eye irritation studies were conducted in order to compare the properties of unbuffered, non-isotonic solutions of PVP-I at pH 4 (Example 13) and unbuffered isotonic PVP-I solutions at pH 4 (Example 14) to isotonic solutions of PVP-I buffered to a pH of 5.6 (Comparative Example C; not stable). In the same study, rabbit eye irritation studies were conducted with a saline solution control and two commercially available products, Neosporin ® and Herplex ®. The formulations for Examples 13 and 14, as well as Comparative Example C are set forth in Table 14 below:

TABLE 14

| Example<br>Ingredient | C<br>% | 13<br>% | 14<br>% |
|---|---|---|---|
| PVP-I | 0.3* | 0.3* | 0.3* |
| Igepal Co-630 | 0.004 | 0.004 | 0.004 |
| Methocel E4M | 0.5 | 0.5 | 0.5 |
| Sodium Chloride | 0.50 | 0.0 | 0.90 |
| Monobasic Sodium Phosphate | 0.76 | 0.0 | 0.0 |
| Dibasic Sodium Phosphate | 0.47 | 0.0 | 0.0 |
| Sodium Hydroxide (5%) | qs to pH 5.6 | qs to pH 4.0 | qs to pH 4.0 |
| Purified water | qs to 100 | qs to 100 | qs to 100 |

*Plus a 20% overage, which is the maximum USP allowable overage.

The results showed that the unbuffered solutions of Examples 3 and 14 at pH 4 (both isotonic and non isotonic) were non-irritating, as was the buffered solution of Comparative Example C. This result was not expected due to the low pH of the PVP-I solution. Rather, it was expected that only PVP-I solutions above pH 5 would to be non-irritating.

In the same study, a rabbit eye irritation study was conducted with the PVP-I solution of Example 12 (0.6% PVP-I solution; 0.06% available iodine). This solution was also found to be non-irritating.

Finally, in Example 15, a randomized paired comparison comfort evaluation was conducted in 30 normal human volunteers with a solution of stabilized, unbuffered isotonic 0.3% PVP-I having the formulation provided for Example 14, with Garamycin ® ophthalmic solution and Sodium Sulamyd ® ophthalmic solution. The results of this study revealed that there was statistically no significant differences in the discomfort between all three solutions.

The examples provided above are not meant to be exclusive. Many other variations of the present invention would be obvious to those skilled in the art, and are contemplated to be within the scope of the appended claims.

What is claimed is:

1. A stabilized non-irritating ophthalmic solution comprising an iodophor solution containing a microbicidal effective amount of available iodin ions of from about 0.03% to about 0.06%, and an alkalinizing agent in an amount effective to maintain said amount of available iodine ions at a minimum of about 85% and a maximum of 120% of an initial amount of said available iodine, for about three months under accelerated aging conditions or for about three years at room temperature, when said ophthalmic solution is stored in a substantially non-permeable container, said alkalinizing agent in said effective amount being non-toxic and non-irritating, said ophthalmic solution being nonbuffered and therefore stable and non-irritating.

2. The ophthalmic solution of claim 1, wherein said iodophor solution comprises povidone-iodine.

3. The ophthalmic solution of claim 1, wherein said alkalinizing agent is selected from the group consisting of sodium hydroxide, potassium hydroxide, sodium bicarbonate, disodium phosphate, and mixtures of the foregoing.

4. The ophthalmic solution of claim 1, wherein said alkalinizing agent comprises sodium hydroxide.

5. The ophthalmic solution of claim 4, wherein said alkalinizing agent comprises a sufficient amount of sodium hydroxide to adjust the pH of solution to an initial value from about to about 6.5.

6. The ophthalmic solution of claim 1 which has a pH from about 2 to about 4.5.

7. The ophthalmic solution of claim 3 which is isotonic to human lacrimal fluid.

8. The ophthalmic solution of claim 5, further comprising an effective amount of sodium chloride to render said solution isotonic to human lacrimal fluid.

9. An iodophor solution stable according to U.S.P. standards, comprising a microbicidal effective amount of available iodine ions which in said amount is insufficient by itself to render said iodophor solution stable according to U.S.P. standards, and an alkalinizing agent in an amount effective to maintain said amount of available iodine ions at a minimum of about 85% and a maximum of 120% of an initial amount of said available iodine for about three months at a temperature of about 37° C., or for about three years at about room temperature, when said solution is stored in a substantially nonpermeable container, said solution being non-buffered.

10. The solution of claim 9, wherein said iodophor comprises PVP- and said alkalinizing agent is selected from the group consisting of sodium hydroxide, potassium hydroxide, sodium bicarbonate, disodium phosphate, and mixtures of any of the foregoing.

11. A microbicidal ophthalmic solution, comprising
povidone-iodine solution in a microbicidal sufficient quantity to initially provide said ophthalmic solution with from about 0.03% to about 0.06% available iodine ions,
a sufficient quantity of an alkalinizing agent to provide said ophthalmic solution with an initial pH of about 2 to about 6.5, such that said solution is rendered stable according to U.S.P. standards when stored in glass, said quantity of alkalinizing agent being non-toxic and non-irritating to the human eye, and
said ophthalmic solution being isotonic to human lacrimal fluid, said ophthalmic solution being non-buffered, non-irritating, and stable.

12. The ophthalmic solution of claim 11, wherein said alkalinizing agent is selected from the group consisting of sodium hydroxide, potassium hydroxide, sodium bicarbonate, disodium phosphate, and mixtures in its place.

13. The ophthalmic solution of claim 12 which has a pH from about 2 to about 6.5.

14. The ophthalmic solution of claim 12 which has a pH from about 4 to about 4.5.

15. The stabilized iodophor solution, comprising a microbicidal effective amount of available iodine ions which in said amount is insufficient by itself to render said iodophor solution stable, and an alkalinizing agent in an amount effective to maintain said amount of available iodine ions at a minimum of about 85% and a maximum of 120% of an initial amount of said available iodine for about one month at a temperature of about 37° C. when said solution is stored in a glass container, said solution being non-buffered.

16. The stabilized iodophor solution of claim 15 which initially comprises from about 0.12% PVP-I to about 0.72% PVP-I.

17. The stabilized iodophor solution of claim 15 which is non-irritating to the human eye.

18. A method of preparing a microbicidal ophthalmic solution comprising povidone-iodine which is stable according to U.S.P. standards when stored in a glass container, comprising providing povidone-iodine in an effective amount of available iodine ions to render said solution microbicidal but which in said effective amount does not render said solution stable, and adding a suitable alkalinizing agent in an amount effective to maintain said amount of available iodine ions at a minimum of about 85% and a maximum of 120% of an initial amount of said available iodine ions for about three months at a temperature of about 37° C., or for about three years at about room temperature, when said solution is stored in a substantially nonpermeable container, such that said alkalinizing agent in said effective amount is non-toxic and non-irritating, said solution being non-buffered.

19. The method of claim 18, further comprising adding an effective amount of sodium chloride to render said solution isotonic to human lacrimal fluid.

20. The product produced according to claim 18.

21. A method of preparing a non-irritating, microbicidal ophthalmic solution comprising povidone-iodine which is stable according to U.S.P. standards when stored in a glass container, comprising providing povidone-iodine in a sufficient quantity to initially provide said ophthalmic solution from about 0.03% to about 0.06% available iodine ions, and adding a suitable alkalinizing agent in an amount effective to maintain said amount of available iodine at a minimum of about 85% and a maximum of 120% of an initial amount of said available iodine ions for about three months at a temperature of about 37° C., or for about three years at room temperature, when said solution is stored in a substantially nonpermeable container.

22. The product according to claim 21.

23. A process for treating the eye with a microbicidal treatment which is table according to U.S.P. standards, comprising preparing a povidone-iodine solution having an effective amount of available iodine ions to render said solution microbicidal but which in said amount does not render said solution stable, adding a suitable alkalinizing agent in an amount effective to maintain said amount of available iodine ions at a minimum of about 85% and a maximum of 120% of an initial amount of said available iodine ions for about three months under accelerated aging conditions or for about three years at about room temperature, when said solution is stored in a substantially nonpermeable container, said effective amount of said alkalinizing agent being non-toxic and non-irritating, said solution being non-buffered, rendering said solution isotonic to human lacrimal fluid, storing said solution in a substantially nonpermeable container for at least three weeks, and thereafter placing a medicinally effective amount of said solution onto a human eye.

* * * * *